United States Patent
Sang et al.

(10) Patent No.: US 8,466,211 B2
(45) Date of Patent: Jun. 18, 2013

(54) ONE-COMPONENT SELF-ETCHING ADHESIVE

(75) Inventors: Junjie Sang, Magnolia, DE (US); Huaibing Liu, Dover, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/592,603

(22) Filed: Nov. 30, 2009

(65) Prior Publication Data
US 2012/0172488 A1   Jul. 5, 2012

Related U.S. Application Data

(63) Continuation of application No. 12/284,854, filed on Sep. 25, 2008, now abandoned, which is a continuation of application No. 11/545,669, filed on Oct. 10, 2006, now abandoned, which is a continuation of application No. 11/432,928, filed on May 12, 2006, now abandoned, which is a continuation of application No. 11/402,127, filed on Apr. 10, 2006, now abandoned, which is a continuation of application No. 11/244,937, filed on Oct. 6, 2005, now abandoned.

(60) Provisional application No. 60/618,649, filed on Oct. 14, 2004.

(51) Int. Cl.
*A61K 6/083* (2006.01)
*C08F 2/50* (2006.01)

(52) U.S. Cl.
USPC ........... 523/116; 523/118; 433/228.1; 522/47

(58) Field of Classification Search
USPC ................. 523/116, 118; 433/228.1
See application file for complete search history.

(56) References Cited

U.S. PATENT DOCUMENTS

| | | |
|---|---|---|
| 4,372,836 A | 2/1983 | Schmitt et al. |
| 4,389,497 A | 6/1983 | Schmitt et al. |
| 4,503,169 A | 3/1985 | Randklev |
| 4,544,359 A | 10/1985 | Waknine |
| 4,602,076 A | 7/1986 | Ratcliffe et al. |
| 4,636,533 A | 1/1987 | Janda et al. |
| 4,640,936 A | 2/1987 | Janda et al. |
| 4,674,980 A | 6/1987 | Ibsen et al. |
| 4,696,955 A | 9/1987 | Kuhlmann |
| 4,707,504 A | 11/1987 | Walkowiak et al. |
| 4,721,735 A | 1/1988 | Bennett et al. |
| 4,746,686 A | 5/1988 | Waller |
| 4,767,798 A | 8/1988 | Gasser et al. |
| 4,820,744 A | 4/1989 | Kubota et al. |
| 4,906,446 A | 3/1990 | Engelbrecht et al. |
| 4,959,297 A | 9/1990 | Palazzotto |
| 4,966,934 A | 10/1990 | Huang et al. |
| 5,004,501 A | 4/1991 | Faccioli et al. |
| 5,033,650 A | 7/1991 | Colin et al. |
| 5,091,441 A | 2/1992 | Omura |
| 5,130,348 A | 7/1992 | Zahler et al. |
| 5,264,513 A | 11/1993 | Ikemura et al. |
| 5,321,053 A | 6/1994 | Hino et al. |
| 5,376,691 A | 12/1994 | May et al. |
| 5,554,665 A | 9/1996 | Tateosian et al. |
| 5,658,963 A | 8/1997 | Qian et al. |
| 5,739,177 A | 4/1998 | Ohno et al. |
| 5,866,631 A | 2/1999 | Nakagawa et al. |
| 5,973,022 A | 10/1999 | Lu et al. |
| 6,071,983 A | 6/2000 | Yamamoto et al. |
| 6,114,408 A | 9/2000 | Dickens |
| 6,147,137 A | 11/2000 | Jia |
| 6,174,935 B1 | 1/2001 | Matsunae et al. |
| 6,191,190 B1 | 2/2001 | Blackwell et al. |
| 6,214,101 B1 | 4/2001 | Nakaseko |
| 6,245,872 B1 | 6/2001 | Frey et al. |
| 6,288,138 B1 | 9/2001 | Yamamoto et al. |
| 6,372,816 B1 | 4/2002 | Walz et al. |
| 6,387,979 B1 | 5/2002 | Hino |
| 6,387,982 B1 | 5/2002 | Blackwell |
| 6,440,519 B1 | 8/2002 | Takase et al. |
| 6,458,869 B1 | 10/2002 | Antonucci et al. |
| 6,482,871 B1 | 11/2002 | Aasen et al. |
| 6,592,372 B2 | 7/2003 | Jia et al. |
| 6,649,669 B2 | 11/2003 | Dickens |
| 6,660,784 B2 | 12/2003 | Ibaragi et al. |
| 6,759,449 B2 | 7/2004 | Kimura et al. |
| 6,815,470 B2 | 11/2004 | Ibaragi et al. |
| 8,022,114 B2 * | 9/2011 | Sang et al. ............. 523/118 |
| 2002/0156152 A1 * | 10/2002 | Zhang et al. ............ 523/115 |
| 2003/0055124 A1 | 3/2003 | Klee et al. |
| 2003/0092788 A1 | 5/2003 | Galstian et al. |
| 2003/0171450 A1 | 9/2003 | Wang et al. |
| 2003/0186196 A1 | 10/2003 | Wang et al. |
| 2003/0187092 A1 | 10/2003 | Fujiwara |
| 2003/0207960 A1 | 11/2003 | Jia |
| 2004/0006154 A1 | 1/2004 | Ibaragi et al. |
| 2005/0009946 A1 | 1/2005 | Oguri et al. |

FOREIGN PATENT DOCUMENTS

| | | |
|---|---|---|
| EP | 0363903 A2 | 4/1990 |
| EP | 0948956 A2 | 10/1999 |
| EP | 1051961 A1 | 11/2000 |
| EP | 1346717 A1 | 9/2003 |
| EP | 1402872 A1 | 3/2004 |
| EP | 1502569 A1 | 2/2005 |
| WO | 03013444 A1 | 2/2003 |
| WO | 2004100900 A1 | 11/2004 |
| WO | 2006044223 A1 | 4/2006 |

\* cited by examiner

*Primary Examiner* — Tae H Yoon
(74) *Attorney, Agent, or Firm* — Leana Levin; Douglas J. Hura; David A. Zdurne

(57) ABSTRACT

A one-part, self-etching dental adhesive having improved performance such as adhesion performance with a simple one-coat application, without the need of separate acid-etching, a priming pre-treatment, or bonding step. The invention provides such improvements due to a function of the pH balance of the system in combination with an acid stable photoinitiating system. More specifically, the performance and pH balance is achieved through the employment of a hydrolytically stable, acidic, high-strength adhesive monomer (such as PENTA), with a stable, bifunctional, hydrophilic monomer (such as AHPMA) that yields greater crosslinking.

2 Claims, 2 Drawing Sheets

ONE-COMPONENT SELF-ETCHING ADHESIVE

RELATED APPLICATIONS

This application is a continuation of U.S. application Ser. No. 12/284,854 (now abandoned) filed Sep. 25, 2008 which is a continuation of U.S. application Ser. No. 11/545, 669 (now abandoned) filed Oct. 10, 2006 which is a continuation of U.S. application Ser. No. 11/432,928 (now abandoned) filed May 12, 2006, which is a continuation of U.S. application Ser. No. 11/402,127 (now abandoned) filed Apr. 10, 2006, which is a continuation of U.S. application Ser. No. 11/244,937 (now abandoned) filed Oct. 6, 2005 which claims benefit of U.S. Provisional Application Ser. No. 60/618,649 filed Oct. 14, 2004.

TECHNICAL FIELD

A one-part, self-etching dental adhesive having improved performance such as adhesion performance with a simple one-coat application, without the need of separate acid-etching, a priming pre-treatment, or bonding step. The invention provides such improvements due to a function of the pH balance of the system in combination with an acid stable photoinitiating system. More specifically, the performance and pH balance is achieved through the employment of a hydrolytically stable, acidic, high-strength adhesive monomer (such as PENTA), with a stable, bifunctional, hydrophilic monomer (such as AHPMA) that yields greater crosslinking.

BACKGROUND OF THE INVENTION

Typically, the procedure for dental composite restorations using a total etch adhesive involves acid etching the tooth using phosphoric acid followed by water rinsing and drying. Subsequently, a primer is applied and dried followed by the application of a bonding agent, which is light cured. Finally, the composite restoration is applied, cured and polished. Overall, there are many steps to complete a dental restoration. Unfortunately, with each additional step the process becomes more difficult increasing the risk for failure. In general, the primary goal of this project is to reduce the number of steps associated with the application of the dental adhesive.

In order to accomplish this objective, the number of components to be used for priming and bonding were combined into one-bottle as exemplified by the Prime & Bond® brand adhesive (Dentsply). However, etching must still be conducted prior to the application and curing of the single component priming. The process is further simplified by combining the priming and etching into a one-component self-etching system. For example, ClearFil SE Bond (Kuraray) is a 2-component system, which consists of a self-etching primer and bonding liquid. In this 2-step system the self-etching primer is applied followed by the application of the bonding agent.

ClearFil SE Bond is indicated for direct light cured composite restoration bonding only. For indirect restoration bonding, Kuraray recommends using ClearFil Liner Bond 2V that is a multi-component (Primers A and B, Bond Liquid A and B) which involves a multi-step application for self-etching adhesive system.

Similarly, Adper Prompt L-Pop (3M ESPE), a 2-component/one-pack/one-step self-etching priming adhesive, is supplied in a unit dose blister package that consists of two-predosed compartments, for the two liquids A and B. Prompt L-Pop is only indicated for bonding direct, light cured composite restorations.

The 1P-SEA product developed at L.D. Caulk further simplifies the technique for applying dental adhesives by incorporating the etching, priming and bonding components into a single component bottle or unit dose package. More specifically, the application technique is reduced from the complex series of events previously described to apply, dry and cure. The Caulk 1P-SEA is differentiated from the only currently marketed single component self-etching adhesive (i-Bond Heraeus Kulzer), through chemistry (see Table 1 for preferred formulation and raw material ranges) and performance (see Tables 2-7). It exhibits performance (microleakage and shear bond strength) which is superior to i-Bond and comparable to the leading 2-component systems available in the dental market.

Ref. U.S. Pat. No. 6,387,979 by K. Hino (Kuraray Co. Ltd., Japan), issued May 14, 2002.

Abstract: A tooth treated with a bonding composition with high initial bonding strength and good bonding durability comprising a mixture of polymerizable compound having an acid group, a water-soluble film-forming agent, water, and a curing agent, in which the calcium salt of the acid is insoluble in water, and the film-forming agent is a polymerizable compound miscible with a physiological saline solution, does not require any pre-treatment such as acid-etching or priming treatment.

This patent states that the active ingredients of the composition in a single package may degrade or polymerize while stored. To prevent this, the constituent ingredients of the composition may be divided into two or more parts. The plural parts are separately packaged and stored in different packages. For their use, the plural parts taken out of the individual packages may be applied to one and the same object in sequence; or they may be blended into one mixture just before use.

SUMMARY OF THE INVENTION

Figure 1:
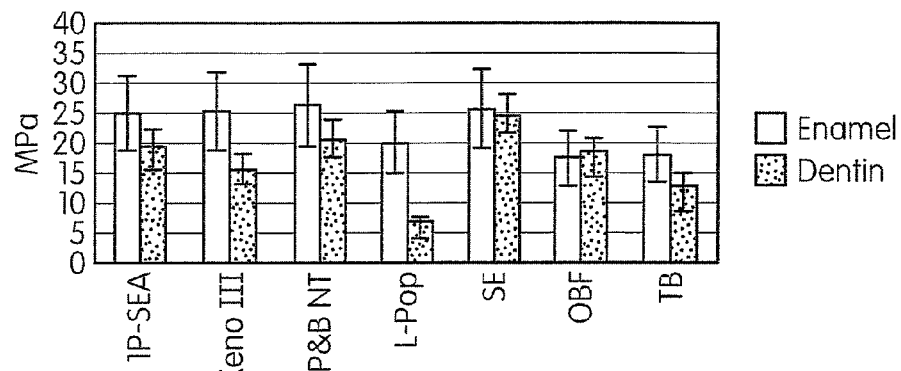
FIG. 1 compares that 24 hour bond strength of the composite disclosed herein to human enamel and dentin with various self-etching adhesive.
Figure 2:
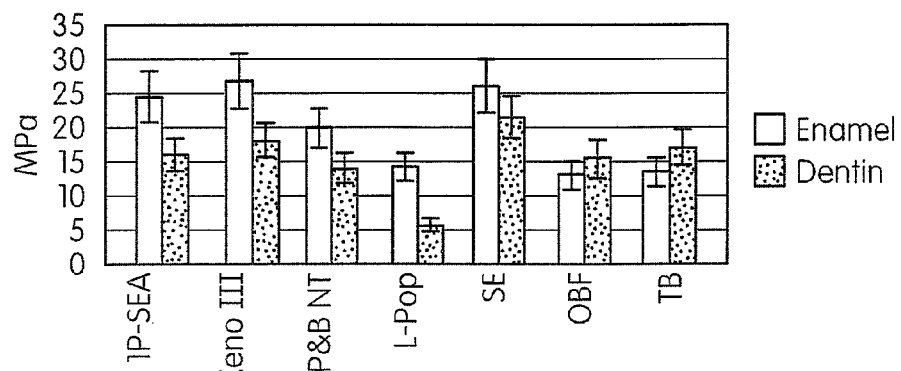
FIG. 2 compares thermal cycled bond strength of the composite disclosed herein to human enamel and dentin with various self-etching adhesives.
Figure 3:
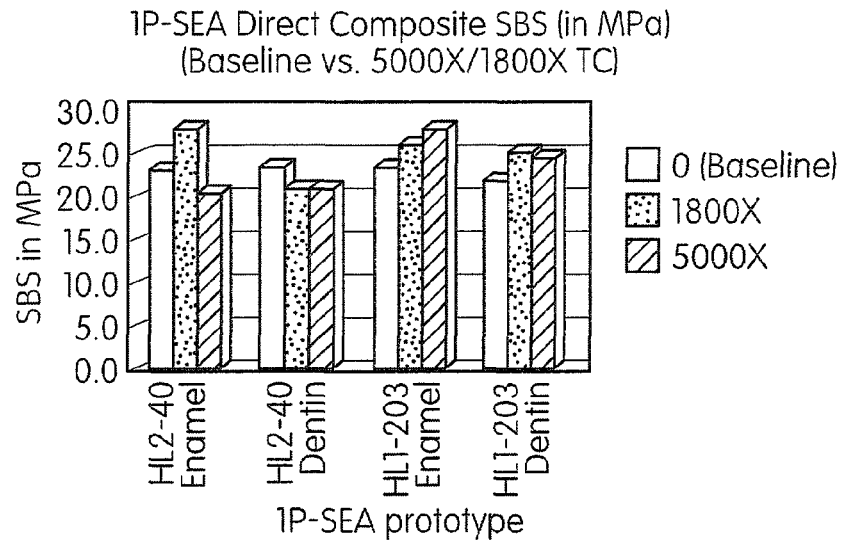
FIG. 3 compares thermal cycled enamel and dentin to composite use the self-etching adhesive disclosed herein.

1P-SEA materials according to the invention can achieve good adhesion performance with a simple one-coat application, without the need of using phosphoric acid tooth gel.

PREFERRED EMBODIMENTS FOR CARRYING OUT THE INVENTION

For One-component Visible Light Cure Self-Etching Adhesive (1P-SEA) according to the invention, it is indicated to bond VLC composite/compomer direct restorations to human teeth substrate (enamel and dentine) without the need of separate acid-etching or priming pre-treatment teeth bonding step. When used with a separate Self-Cure Activator component, the 1P-SEA can also bond for cemented indirect restorations (prefabricated metal/porcelain/composite Inlays/Onlays/Veneers/Crowns/Bridges) to human teeth substrate (enamel and dentine) without separate acid etching or priming pre-treatment step. In addition, 1P-SEA can also be used as a cavity varnish.

onto dentin and/or enamel surfaces to bond direct light cure composite restorations. The 1P-SEA is easily differentiated from the prior art which divides the active ingredients of the composition into two or more parts (in different packages) to avoid composition degradation or polymerization. The

TABLE 1

Prototype Formulation of One-Component Self-Etching Adhesive

| Raw Material | Chemical Name | CAS # | Formulation Ranges | Preferred % Weight |
|---|---|---|---|---|
| UDMA | 2-Methyl-acrylic acid 1-methyl-2-{3,5,5-trimethyl-6-[1-methyl-2-(2-methyl-acryloyloxy)-ethoxycarbonyl amino]-hexylcarbamoyloxy}-ethyl ester | 105883-40-7 | 5-15 | 10.50 |
| PENTA | 2-Methyl-acrylic acid 4-(2-methyl-acryloyloxy)-2,2,3-tris-(2-methyl-acryloyloxymethyl)-3-phosphonooxymethyl-butyl ester | 87699-25-0 | 8-20 | 12.80 |
| HEMA | 2-Methyl-acrylic acid 2-hydroxy-ethyl ester | 868-77-9 | 0-5 | 3.20 |
| AHPMA | 2-Methyl-acrylic acid 3-acryloyloxy-2-hydroxy-propyl ester | 1709-71-3 | 5-15 | 9.50 |
| TMPTMA | 2-Methyl-acrylic acid 2,2-bis-(2-methyl-acryloyloxymethyp-butyl ester | 3290-92-4 | 0-5 | 1.60 |
| L-TPO | (Diphenyl-phosphinoyl)-(2,4,6-trimethyl-phenyl)-methanone | 75980-60-8 | 0.1-2.0 | 0.99 |
| CQ | Bicyclo [2,2,1] heptane-2,3 dione, 1,1,7-trimethyl | 10373-78-1 | 0.05-0.50 | 0.19 |
| DMABN | 4-Dimethylamino-benzonitrile | 1197-19-9 | 0.1-1.2 | 0.79 |
| BHT | Phenol, 2,6-bis (1,1-dimethylethyl-4-methyl) | 128-37-0 | 0.01-0.2 | 0.13 |
| CAF | Hexadecyl-ammonium; fluoride | 3151-59-5 | 0-1.0 | 0.30 |
| Water | Water | 7732-18-5 | 5-20 | 12.60 |
| Acetone | 2-Propanone | 67-64-1 | 20-60 | 47.40 |
| Total | | | | 100 |

Physical Properties and Characteristics

True one-component self-etching bonding agent in both bottle and unit dose package No mixing or rinsing requirement prior to application One-coat/One-step simple and robust technique VLC direct bond strength equal or better than Xeno III and other 2-component competitors Indirect bond strength (when used with separate SCA component) equivalent to that of P&B NT/SCA Dual Cure adhesive Low film thickness (<15 μm)

Fluoride releasing

Microleakage at least as good as the current P&B NT and Xeno III systems

Comparison to Competitive Products

In Vitro shear bond strength before and after thermocycling was tested on 1P-SEA and other dental adhesives. The data is shown in FIGS. 1-4. Seven dental adhesives were selected: 1P-SEA (Dentsply), Xeno III (Dentsply), Prime & Bond NT (P&B NT, Dentsply), Prompt L-Pop (L-Pop, 3M ESPE), ClearFil SE Bond (SE, Kuraray), One-up Bond F (OBF, Tokuyama), i-Bond (IB, Heraeus Kulzer).

In general, the previous adhesion data and graphs indicate that the 1P-SEA prototypes exhibit comparable performance to the leading currently marketed, 2-component, self-etching adhesive products.

The single-component self-etching adhesive (1P-SEA) prototype demonstrates an improvement to the existing commercial self-etching adhesive products. The new self-etching adhesive material achieves good adhesion performance with a simple one-coat application, without the need of separate acid-etching, a priming pre-treatment, or bonding step.

1P-SEA is a light cured self-etching adhesive contained in a single package (bottle or single unit-dose) which is applied 1P-SEA is designed to overcome the single package storage stability issues through optimization of the formulation to provide competitive self-etching adhesion performance without presenting the stability issues commonly associated with other self-etching adhesives contained in a single package.

The improved performance in conjunction with other feature/benefits previously identified in the 1P-SEA is a function of the pH balance of the system in combination with an acid stable photoinitiating system. More specifically, the performance and pH balance is achieved primarily through the employment of the hydrolytically stable, acidic, high-strength adhesive monomer (PENTA), with a stable, bifunctional, hydrophilic monomer (AHPMA) that yields greater crosslinking.

Optimally, a minimal amount of water has been incorporated into a water-miscible polar aprotic organic solvent, e.g., acetone to facilitate etching. In addition, micro- or nanosized fillers and fluoride-releasing agents can also be incorporated into the 1P-SEA composition to enhance performance and inhibit secondary caries through releasing fluoride.

Optionally, a separate self-curing activator component can be utilized with the 1P-SEA to facilitate the use of this product for indirect self cure applications (prefabricated metal/porcelain/composite Inlays/Onlays/Veneers/Crowns/Bridges). The 1P-SEA exhibits superior bonding performance over other single component self-etching (prior art) products. More specifically, the 1P-SEA yields high initial and sustained long-term bonding performance (enamel bond strength≧20 MPa and dentin bond strength MPa). As previously discussed, the new 1P-SEA product achieves good adhesion with a simple "one-coat" one-step application technique, without separate acid-etching or priming.

The bonding performance of the 1P-SEA is sustained after excessive thermal stressing (5000 cycles at 55° C.). In addition, this product has demonstrated excellent shelf storage stability withstanding 3 weeks at 50° C. without a significant decrease in performance while—Bond (Kulzer), the only commercial single-component SEA gelled after storage at 50 248 C for a week. In comparison with current commercial self-etching adhesive products, the 1P-SEA exhibits comparable or superior bonding performance, storage stability and shelf life.

Table 5 shows 24-hr dentin shear bond strength of 1P-SEA after storage at different temperatures and for different time duration. Table 6 compares bond strength of three different experimental 1P-SEA differing only in aromatic amines. DHEPT and EDAB are two most commonly used co-initiators for CQ. The formulations containing either DHEPT or EDAB did not lead to acceptable balanced properties. Only the formulation incorporating DMABN exhibits the superior balance of bond strength, storage stability and compatibility with different curing lights, e.g., QTH light and LED light. DMABN is the first time ever used in any dental adhesive.

TABLE 5

24 hr Dentin SBS of 1P-SEA in MPa (Mean ± Stdev.)

| Time (week) | 37° C. | 45° C. | 50° C. | 60° C. |
|---|---|---|---|---|
| 0 | 17.6 ± 5.2 | 17.6 ± 5.2 | 17.6 ± 5.2 | 17.6 ± 5.2 |
| 1 | NT | NT | NT | 18.8 ± 7.5 |
| 1.5 | NT | NT | NT | 17.5 ± 4.6 |
| 2 | NT | NT | 17.8 ± 5.8 | 12.3 ± 4.2 |
| 3 | NT | 19.4 ± 9.2 | 18.1 ± 7.2 | 10.8 ± 3.5 |
| 3.5 | NT | 16.6 ± 3.8 | 17.9 ± 6.8 | NT |
| 4 | NT | 17.8 ± 5.1 | 8.2 (2.2) | NT |
| 6 | 16.8 ± 7.0 | 15.0 ± 5.6 | NT | NT |
| 7 | NT | 16.7 ± 5.0 | NT | NT |
| 8 | 24.0 ± 2.8 | 17.5 ± 5.2 | NT | NT |
| 10 | 15.5 ± 4.8 | 7.3 ± 3.9 | NT | NT |
| 11 | 17.5 ± 4.6 | NT | NT | NT |
| 12 | 12.7 ± 3.8 | NT | NT | NT |

TABLE 6

24 hr Shear Bond Strength of 1P-SEA Containing Different Co-initiators

| Sample I.D. | | | 1P-SEA containing DMABN | 1P-SEA containing DHEPT | 1P-SEA containing EDAB |
|---|---|---|---|---|---|
| Human Dentin SBS (MPa): Mean (SD) | RT stored 50° C. 3 weeks | QTH Light LED Light QTH Light LED Light | 23.2 (3.9) 22.0 (4.0) 15.3 (4.2) 15.8 (6.1) | NT NT NT NT | 17.0 (7.5) 15.6 (5.7) 14.5 (6.9) 16.8 (6.8) |
| Human Enamel SBS (MPa): Mean (SD) | RT stored 50° C. 3 weeks | QTH Light LED Light QTH Light LED Light | 26.4 (5.3) 32.0 (3.0) 26.7 (5.3) 35.3 (7.9) | 13.5 (6.7) NT NT NT | 32.7 (7.2) 30.1 (7.3) 7.6 (2.0) 24.8 (13.3) |

Figure 4:
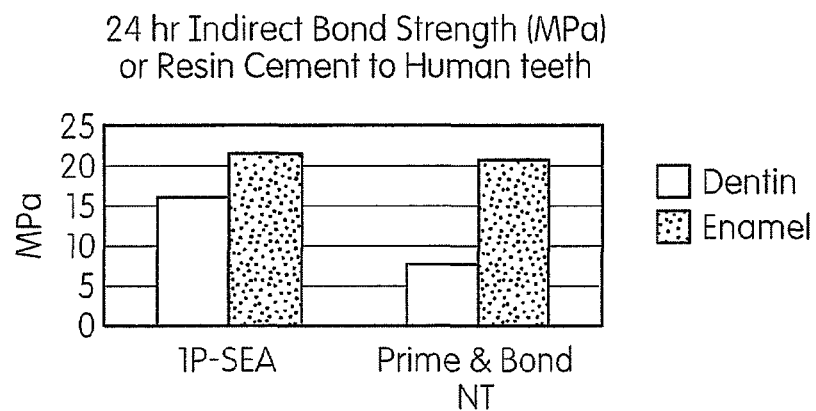
FIG. 4 compares the 24 hour indirect bond strength of a self-cure adhesive and a resin cement to human teeth.

SEA exhibits excellent shear bond strength on both dentin and enamel when used with Self-Cure Activator to bond resin cements (i.e. Calibra). FIG. 4 illustrates that SEA has improved bonding performance in comparison to Prime & Bond NT for bonding Calibra to tooth substrates.

Packaging Addendum

The minimum design specifications for SEA require a unit-dose packaging format similar to the system currently used for Prime & Bond® NT. Dentsply International, under U.S. Pat. No. 6,372,816 has patented this system (packaging), Waltz, et al., as of Apr. 16, 2002. The ideal requirements for packaging are defined as "integral brush unit-dose" (IB unit-dose). Patent application Ser. No. 10/668,946, Pierson, et al., Sep. 23, 2003, has been submitted for the IB unit-dose packaging under case number LDC-922-E.

What is claimed is:

1. A one-part, self-etching dental adhesive comprising 5 to 15% by weight 2-methyl-acrylic acid 1-methyl-2-{3,5,5-trimethyl-6-[1-methyl-2-(2-methyl-acryloyloxy)-ethoxycarbonyl amino]-hexylcarbamoyloxy}-ethyl ester; 8 to 20% by weight 2-methyl-acrylic acid 4-(2-methyl-acryloyloxy)-2,2,3-tris-(2-methyl-acryloyloxymethyl)-3-phosphonooxym-ethyl-butyl ester; 0 to 5% by weight 2-methyl-acrylic acid 2-hydroxy-ethyl ester; 5 to 15% by weight 2-methyl-acrylic acid 3-acryloyloxy-2-hydroxy-propyl ester; 0 to 5% by weight 2-methyl-acrylic acid 2,2-bis-(2-methyl-acryloyloxymethyl-butyl ester; 0.1 to 2.0% by weight diphenyl (2,4,6-trimethylbenzoyl)phosphine oxide; 0.05 to 0.50% by weight camphorquinone; 0.1 to 1.2% by weight dimethylaminobenzonitrile; 0.01 to 0.2% by weight 2,6-bis(1,1-dimethylethyl-4-methyl)phenol; 0 to 1.0% by weight hexadecyl-ammonium fluoride; 5 to 20% by weight water; and 20 to 60% by weight acetone.

2. A one-part, self-etching dental adhesive comprising 10.5% by weight 2-methyl-acrylic acid 1-methyl-2-{3,5,5-trimethyl-6-[1-methyl-2-(2-methyl-acryloyloxy)-ethoxycarbonyl amino]-hexylcarbamoyloxy}-ethyl ester; 12.8% by weight 2-methyl-acrylic acid 4-(2-methyl-acryloyloxy)-2,2,3-tris-(2-methyl-acryloyloxymethyl)-3-phosphonooxym-ethyl-butyl ester; 3.2% by weight 2-methyl-acrylic acid 2-hydroxy-ethyl ester; 9.5% by weight 2-methyl-acrylic acid 3-acryloyloxy-2-hydroxy-propyl ester; 1.6% by weight 2-methyl-acrylic acid 2,2-bis-(2-methyl-acryloyloxymethyl-butyl ester; 0.99% by weight diphenyl (2,4,6-trimethylbenzoyl)phosphine oxide; 0.19% by weight camphorquinone; 0.79% by weight dimethylaminobenzonitrile; 0.13% by weight 2,6-bis(1,1-dimethylethyl-4-methyl)phenol; 0.3% by weight hexadecyl-ammonium fluoride; 12.6% by weight water; and 47.4% by weight acetone.

* * * * *